United States Patent [19]

Stetter et al.

[11] 4,014,889

[45] Mar. 29, 1977

[54] PROCESS FOR PREPARING KETONES

[75] Inventors: Hermann Stetter, Aachen-Laurensberg; Manfred Schreckenberg, Aachen, both of Germany

[73] Assignee: Bayer Aktiengesellschaft, Leverkusen, Germany

[22] Filed: June 11, 1975

[21] Appl. No.: 586,118

Related U.S. Application Data

[62] Division of Ser. No. 424,231, Dec. 12, 1973, abandoned.

[52] U.S. Cl. .................. 260/294.9; 260/289 D; 260/289 R; 260/297 R; 260/304 R; 260/309; 260/309.2; 260/319.1; 260/326.5 J; 260/330 S; 260/332.3 R; 260/343.2 R; 260/347.8; 260/465 R; 260/465 F; 260/465 G; 260/475 SC; 260/476; 260/590 R; 260/590 D; 260/590 E; 252/522; 424/65

[51] Int. Cl.² .................................. C07D 213/50

[58] Field of Search ....... 260/465 R, 590 R, 297 R, 260/294.9, 590 E, 590 D, 476, 475 SC, 465 F, 465 G, 347.8, 294.9, 332.3 R

[56] References Cited

FOREIGN PATENTS OR APPLICATIONS 2,262,343  6/1974  Germany

OTHER PUBLICATIONS

Stetter et al "Chem. Abstracts" vol. 78 No. 110812j (2-1973).
Stetter et al "Chem. Abstracts" vol. 79 No. 66102x (9-1973).
Noller "Chemistry of Organic Compounds" 3rd ed. (1965) p. 243.

*Primary Examiner*—Henry R. Jiles
*Assistant Examiner*—R. W. Ramsuer
*Attorney, Agent, or Firm*—Burgess, Dinklage & Sprung

[57] ABSTRACT

Ketones are prepared by reacting an aromatic or heterocyclic aldehyde in the presence of a cyanide ion with an unsaturated compound having the formula (I):

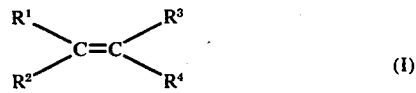

wherein
$R^1$, $R^2$ and $R^3$ are the same or different and are selected from the group of hydrogen, optionally substituted aliphatic, cycloaliphatic, araliphatic, aromatic, heterocyclic and carboxylic acid ester and
$R^4$ is nitrile (CN), —CO—$R^5$ or —CO—O$R^5$ wherein
$R^5$ is selected from the group of optionally substituted aliphatic, cycloaliphatic, araliphatic, aromatic and heterocyclic and
$R^1$ and $R^2$ and/or $R^1$ and $R^3$ and/or $R^2$ and $R^5$ or $R^3$ and $R^5$ together with the carbon atoms to which they are attached as substituents may also form a carbocyclic or heterocyclic ring.

Ketones prepared according to the process of the invention have the formula:

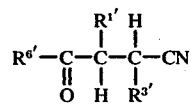

wherein
$R^{1'}$ and $R^{3'}$ are identical or different and are selected from the group of hydrogen, lower alkyl having up to 3 C-atoms and optionally substituted phenyl; and
$R^{6'}$ is optionally substituted phenyl or a pyridyl.

9 Claims, No Drawings

PROCESS FOR PREPARING KETONES

This is a division of application Ser. No. 424,231, filed Dec. 12, 1973 now abandoned.

BACKGROUND

This invention relates to a process or preparing ketones from aromatic or heterocyclic aldehydes and unsaturated compounds by reacting them in the presence of cyanide ions.

SUMMARY

It has been found that ketones are obtained in high yeilds when aromatic or heterocyclic aldehydes are reacted with unsaturated compounds of the following general formula, in the presence of cyanide ions.

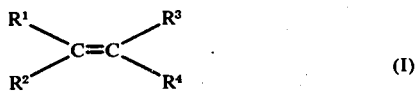

in which $R^1$, $R^2$ and $R^3$ are identical or different and denote hydrogen, an optionally substituted aliphatic, cycloaliphatic, araliphatic, aromatic or heterocyclic group or a carboxylic acid ester group and $R^4$ represents the nitrile group (CN), —CO— $R^5$ or —CO—OR$^5$ group in which $R^5$ denotes an optionally substituted aliphatic, cycloaliphatic, araliphatic, aromatic or heterocyclic group, and $R^1$ and $R^2$ and/or $R^1$ and $R^3$ and/or $R^2$ and $R^5$, or $R^3$ and $R^5$, together with the carbon atoms to which they are attached as substituents, may also form a carbocyclic or heterocyclic ring.

DESCRIPTION

The process according to the invention is generally carried out at temperatures of between $-10°$ and $100°$ C, preferably at about $10°$ to $75°$ C and more particularly between $20°$ and $50°$ C.

The aliphatic groups ($R^1$, $R^2$, $R^3$ and $R^5$) may be optionally substituted, straight or branched chain aliphatic groups, preferably alkyl groups, containing up to 12 and preferably up to 6 carbon atoms, for example hexyl, pentyl, butyl, isobutyl, tertiary butyl, propyl, isopropyl, ethyl or methyl groups.

The cycloaliphatic groups ($R^1$, $R^2$, $R^3$ and $R^5$) may contain up to 18 and preferably up to 12 carbon atoms, more especially 5 to 7 carbon atoms. The cyclohexyl group is preferred.

The optionally substituted araliphatic groups ($R^1$, $R^2$, $R^3$ and $R^5$) may contain up to 18 and preferably up to 12 C atoms in which the aliphatic portion preferably contains up to 6 carbon atoms and the aromatic portion is preferably a naphthyl or phenyl group.

The optionally substituted aromatic groups ($R^1$, $R^2$, $R^3$ and $R^5$) may, for example, contain up to 18 C atoms and are preferably phenyl or naphthyl groups.

The optionally substituted heterocyclic groups ($R^1$, $R^2$, $R^3$ and $R^5$) are preferably 5- or 6-membered heterocyclic groups which may be condensed with a benzene ring.

The hetero atoms may be, for example, nitrogen, oxygen or sulphur. the heterocyclic rings may contain one or more hetero atoms which may be identical or different. The following are examples of suitable heterocylic groups: Pyrrole, furna, thiofen, indole, coumaran, thionaphthene, pyridine, pyrone, oxazole, imidazole, benzoxazole, benzimidazole, benzthiazole quinoline and isoquinoline. The heterocyclic ring systems (e.g. those mentioned above) may be partly or completely hydrogenated.

If the groups $R^1$ and $R^2$ and/or $R^1$ and $R^3$ and/or $R^2$ and $R^5$, or $R^3$ and $R^5$ together with the carbon atoms to which they are attached as substituents form a ring, then this ring may be either carbocyclic or heterocyclic and if heterocyclic, the ring systems cover the same range of meanings as defined above for groups $R^1$, $R^2$, $R^3$ and $R^5$. The carbocyclic groups are preferably 5-membered or 6-membered rings, i.e. a cyclophentan or cyclohexane ring which may contain double bonds and must in cases where $R^2$ and $R^5$ together form a ring contain at least one double bond.

The substituents on the optionally substituted aliphatic, cycloaliphatic, araliphatic and/or aromatic groups may be halogen (fluorine, bromine, chlorine or iodine but preferably chlorine), a cyano group, a nitro group, an optionally monosubstituted or disubstituted amino group, an alkyl group preferably containing up to 6 c atoms, an aryl group, preferably a phenyl group, the hydroxyl, alkoxy, alkylthio, carboxylic acid ester and thiocarboxylic acid ester groups with preferably up to 6 C atoms, alkylcarbonyl, arylcarbonyl, alkylthiocarbonyl and arylthiocarbonyl groups.

The aromatic and heterocyclic aldehydes used for the process according to the invention generally correspond to the general formula

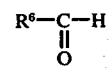 II in which $R^6$ denotes an optionally substituted aromatic or heteocyclic group.

The aromatic groups ($R^6$) may be the same as groups $R^1$, $R^2$, $R^3$ and $R^5$ mentioned above, also as regards the possible substituents.

The heterocyclic groups ($R^6$) may be 5- or 6-membered heterocyclic rings which may be condensed with a benzene ring. The hetero atoms may be, for example, nitrogen, oxygen or sulphur. the heterocyclic rings may contain one or more of these hetero atoms which may be identical or different. The following are examples of heterocyclic groups: Pyrrole, furan, thiophen, indole, coumaran, thionaphthene, pyridine, pyrone, oxazole, imidazole, benzoxazole, benzimidazole, benzthiazole, quinoline, isoquinoline, carbazole, benzofuran and dibenzofuran.

The heterocyclic groups ($R^6$) may be substituted in the same way as the aromatic groups ($R^1$, $R^2$, $R^3$ and $R^5$).

The carboxylic acid ester group may be the group-COOR$^5$ in which $R^5$ has the meaning indicated above.

The reaction is generally carried out as follows:

The aromatic or heterocyclic aldehyde is dissolved in a solvent, a cyanide is added and the mixture is stirred for a short time, during which the temperature of the mixture generally rises slightly.

The unsaturated compound of the general formula I, optionally dissolved in a solvent, is then slowly added with stirring until all of the compound of Formula I has been added. The mixture is then stirred for about the same length of time as taken to add the compound. After the reaction is completed, the reaction product is isolated in a known manner.

It is generally advisable to add water to the reaction mixture for the purpose of separating the cyanide and to remove the organic phase. Depending on the solubility of the solvent and of the reaction product in water, it may be advantageous to extract the aqueous phase with an organic solvent. The reaction product is then isolated in a known manner from the combined organic phases, e.g. by evaporation of the solvent or distillation. When the reaction product has been isolated in this way, it may then be further purified in a known manner, e.g. by recrystallisation, distillation or chromatography.

The reaction is generally carried out in a solvent. Polar solvents are particularly suitable for this purpose, for example methanol, ethanol, isopropanol, dioxane, acetonitrile, dimethylformamide, dimethylsulphoxide or hexamethylphosphoric acid amide.

Dimethylformamide and dimethylsulphoxide are preferred.

The reaction may, however, be carried out without a solvent or an excess of one of the starting materials may be used as the solvent.

It is not essential, although preferable to use anhydrous solvents.

The specific quantity of cyanide ions present during the reaction is not important and even catalytic quantities of less than 1 mol percent, based on the aldehyde, are sufficient. The process according to the invention is generally carried out in the presence of larger quantities of cyanide ions, i.e. about 5 to 100 mols percent, preferably 10 to 75 mols percent and especially about 50 mols percent, based on the aldehyde. Even larger quantities of cyanide ions may be used if desired.

The known cyanides of metals and tetra-alkyl-ammoniumcyanides may be used to provide the cyanide ions. The cyanides of the alkali metals and particularly potassium cyanide and sodium cyanide are preferred.

The cyanides may be used without having first been dried although they are preferrably dried in known manner, e.g. over KOH, before being used.

The aromatic and heterocyclic aldehydes which may be used for the process according to the invention are already known. The following are examples: Benzaldehyde, 4-chloro-benzaldehyde, 2-chlorobenzaldehyde, 4-bromobenzaldehyde, 4-iodobenzaldehyde, 4-fluorobenzaldehyde, 2-, 3- and 4-nitrobenzaldehyde, 2,4-dinitrobenzaldehyde, salicylic aldehyde, 2-, 3- and 4-methoxybenzaldehyde, 4-carbethoxybenzaldehyde, 2-, 3- and 4-methylbenzaldehyde, 2-, 3- and 4-ethylbenzaldehyde, α- and β-naphthaldehyde, furfurol, pyrrol-2-aldehyde, indole-3-aldehyde, carbazole-4-aldehyde, benzofuran-2-aldehyde, thiophen-3-aldehyde, pyrazole-3-aldehyde, imidazole-4-aldehyde, benzimidazole-3- aldehyde, oxazole-4-aldehyde, pyridine-2-aldehyde, pyridine-3-aldehyde, pyridine-4-aldehyde, 2-methyl-pyridine-3-aldehyde, quinoline-5-aldehyde, quinoline-2-aldehyde, isoquinoline-1-aldehyde and uracil-6-aldehyde.

Instead of the free aldehydes, benzoins of the general formula

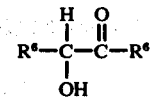

in which R⁶ has the meaning previously defined may be used as staring material since they decompose into free aldehydes under the reaction conditions.

Unsaturated compounds of the general formula I which may be used for the process according to the invention are also already known. The following are examples: Methyl vinyl ketone, phenyl vinyl ketone, β-naphthyl vinyl ketone, benzalacetone, dibenzal acetone, benzalopinacolone, 1-benzalcyclopentanone-(2), benzalacetophenone, 4'-nitro-chalkone, 4'-dimethylamino-chalkone, 2'-hydroxy-4'-methyl-chalkone, β-pyridyl-β-styryl ketone, 3-nitro-chalkone, p-anisalcyclopentanone, furfural-acetone, 1-(α-pyridyl)-3-phenylpropenone-(3), mesityl oxide, cyclopentenone, cyclohexenone, 1-benzal-cyclopentanone-(2); acrylic acid esters, crotonic acid esters, maleic acid esters, cinnamic acid esters, α-pyridyl-acrylic acid esters, furfurylidene acetic acid esters, cyclohexene-(1) -carboxylic acid esters, and p-nitrocinnamic acid esters; acrylonitrile, methacrylonitrile, crotonic acid nitrile, and cyclopentane-(1)-carboxylic acid nitrile.

Instead of α,β-unsaturated ketones corresponding to the general formual I, which are represented by the general formula

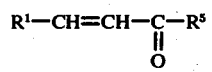

in which

R¹ and R⁵ have the meanings indicated above, may also be used Mannich bases of the general formula

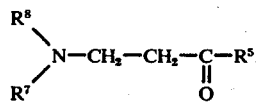

in which

R⁷ and R⁸ are identical or different and denote an aliphatic group containing up to 6 and preferably up to 3 C atoms, in particular the methyl group, or together with the nitrogen atom denote a 5-membered or 6-membered ring and R⁵ has the meaning indicated above, since these Mannich bases react as unsaturated compounds under the reaction conditions and split off the corresponding secondary amine.

The following are examples of such Mannich bases: N,N-Dimethyl-β-benzoyl-ethylamine, N-(3-oxobutyl)-piperidine or N,N-diethyl-β-pivaloyl-ethylamine.

Equimolar quantities of an aldehyde and an unsaturated compound of Formula I react in accordance with the given reaction equation but generally the aldehyde is used in excess. The amount of excess used is optional and generally does not influence the process according to the invention. It would be suitable to use up about 100% excess preferably about one third.

If instead of the aldehyde the corresponding benzoin is used as the starting material, the benzoin is used in half the molar quantity of the aldehyde on account of its equivalence.

The unsaturated compound of Formula I may also be used in excess if desired.

The process according to the invention may be represented by the following reaction scheme using benzaldehyde and acrylonitrile as examples:

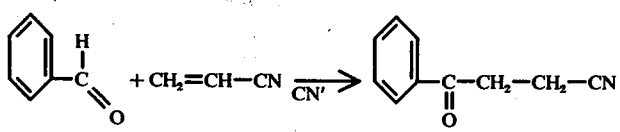

The ketones which can be obtained by the process according to the invention correspond to the general formula

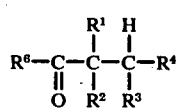

in which
R$^1$, R$^2$, R$^3$, R$^4$ and R$^6$ have the meanings indicated above.

A part of the ketones which correspond to the general formula V are hitherto unknown. Some of the new ketones which can be obtained by the process according to the invention, correspond to the general formula

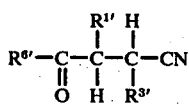

in which
R$^{1'}$ and R$^{3'}$ are identical or different and denote hydrogen, a lower alkyl group having up to 3 C-atoms or an optionally substituted phenylradical and
R$^{6'}$ denotes an optionally substituted phenyl or a pyridyl radical.

A further group of the new compounds corresponds to the general formula

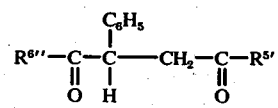

in which
R$^{5'}$ denotes an alkyl radical having up to 3 C-atoms or a phenyl radical, and
R$^{6''}$ denotes an optionally substituted phenyl, a furyl or a pyridyl radical.

The ketones which can be obtained by the process of the invention are valuable intermediate products, preferably for the production of perfumes and can be used as scents.

In the following examples, the percentage sign has been omitted from the figures obtained by elementary analyses.

EXAMPLES

The NaCN used in the following examples was powdered and dried over KOH in a desiccator before use.

The absolute dimethylformamide used in the examples was dried by distillation over calcium hydride.

EXAMPLE 1

320 ml of absolute dimethylformamide, 42.5 g (0.4 mol) of freshly distilled benzaldehyde and 9.8 g (0.2 mol) of sodium cyanide are introduced into a 500 ml 4-necked flask equipped with dropping funnel, stirrer, KOH drying tube and internal thermometer. A week exothermic reaction takes place after the addition of sodium cyanide to the reaction mixture and the temperature rises from 30° to 34° C. The reaction mixture is stirred for 15 minutes at a reaction temperature of 30° C and a solution of 15.9 g (0.3 mol) of freshly distilled acrylonitrile and 80 ml of absolute dimethylformamide is introduced dropwise into the reaction mixture in the course of one hour at the same temperature. Stirring is then continued for ¼ hours at the same temperature. The reaction mixture, which is now very creamy, is poured on to 800 ml of water and vigorously shaken. The aqueous solution is extracted twice with 200 ml of chloroform and twice with 100 ml of chloroform. The combined chloroform solutions are vigorously washed with water and dried over MgSO$_4$ and the chloroform is distilled off. Inoculating crystals are added to the residue. β-Benzoyl-propionitrile then crystallises at once. It is suction filtered and washed with ethanol. 26.6 g of β-benzoylpropionitrile are obtained. M.p.: 69° C.

No further precipitate can be obtained from the mother liquor even by cooling it in a bath of dry ice and acetone. The concentrated mother liquor is therefore vacuum distilled. after which a further quantity of reaction product can be isolated from it.

Yield: 37.6 g (79% of theoretical) of β-benzoylpropionitrile. M.p.: 74° C after recrystallisation from ethanol.

EXAMPLE 2

42.5 g (0.2 mol) of benzoin (m.p.: 131° C), 320 ml of absolute dimethylformamde and 9.8 (0.2 mol) of NaCN (dried) are added together as described in Example 1. A weak exothermic reaction again takes place when NaCN is added to the reaction mixture. A solution of 15.9 g (0.3 mol) of freshly distilled acrylonitrile and 80 ml of absolute dimethylformamide is then slowly added dropwise. The reaction mixture undergoes the same external changes as in the case of the reaction between benzaldehyde and acrylonitrile. The crude product amounting to 62 g is distilled. After distillation of the first running (1.6 g with a faint odour of benzaldehyde), 35.1 g of β-benzoyl-propionitrile are obtained.

B.p: 139° – 143° C/0.5 mm Hg; M.p: 65° 14 66° C.

EXAMPLE 3

200 ml of absolute dimethylformamide and 1.0 g (0.02 mol) of sodium cyanide are introduced into a 500 ml 4-necked flask equipped with two dropping funnels, stirrer, KOH drying tube and internal thermometer. A solution of 56.2 g (0.4 mol) of p-chlorobenzaldehyde and 120 ml of absolute dimethyl formamide are added dropwise to this mixture in the course of ¾ hour at 35° C. A creamy product is formed. Stirring is then continued for 15 minutes.

A solution of 15.9 g (0.3 mol) of freshly distilled acrylonitrile and 80 ml of dimethlformamide is added to this reaction mixture dropwise in the course of 1½ hours at a reaction temperature of 34° to 35° C. Stirring is continued for 1½ hours at the same temperature. A very creamy product again forms towards the end of the reaction. About 1 l of water is added to the reaction mixture and the mixture is then vigorously shaken, a reddish coloured, smeary product precipitating, which is suction filtered.

The mother liquor is extracted twice with 200 ml of chloroform. The chloroform solutions are washed with water and the chloroform is distilled off. 9.2 g of an oily product are obtained from which crystals subsequently precipitate. Since it is not possible to completely separate the suction filtered reaction product by crystallisation, the reaction product is dissolved in chloroform. The chloroform solution is washed with water and dried over $MgSO_4$ and the solvent is then distilled off. The crude product (67.9 g) is distilled. β-p-chlorobenzoyl-propionitrile is obtained with b.p. 178°–182° C/0.5 mm Hg.

A pure product melting at 72° to 73° C is obtained by recrystallisation from ethanol. The product was identified on the basis of the data obtained by analysis and comparison with a sample which had been prepared by a different method (see Soc. 1947, 1193).

EXAMPLE 4

56.2 g (0.4 mol) of p-chlorobenzaldehyde dissolved in 120 ml of absolute dimethylformamide are slowly added dropwise to a mixture of 9.8 g (0.2 mol) of NaCN and 200 ml of dimethylformamide in a manner analogous to Example 3. A solution of 34.3 g (0.3 mol) of freshly distilled ethyl crotonate and 80 ml of DMF is then slowly added dropwise to this reaction mixture in the course of 2½ hours at 35° C.

Stirring is continued for 2½ hours at the same temperature and the reaction mixture is then treated with twice its quantity of water and extracted with chloroform. The combined chloroform solutions are thoroughly washed with water and dried over $MgSO_4$ and the chloroform is distilled off. 79 g of crude product are subjected to distillation.

Yield: 43 g (56% of theoretical) of β-p-chlorobenzoyl butyric acid ethyl ester; B.p. 121° C/0.2 mm Hg; m.p. 34° C. $C_{13}H_{15}O_3Cl$ (254.72) Calculated: C, 61.30; H, 5.94; Found: C, 61.18; H, 5.80.

EXAMPLE 5

28.1 g (0.2 mol) of chlorobenzaldehyde dissolved in 100 ml of dimethylformamide are slowly added dropwise to a mixture of 4.9 g (0.1 mol) of NaCN and 100 ml of absolute dimethylformamide in a manner analogous to Example 3.

A solution of 21.9 g (0.15 mol) of benzalacetone and 100 ml of absolute dimethylformamide is then slowly added dropwise in the course of 4 hours.

Stirring is continued for 4 hours at the same temperature and the reaction mixture is then treated with twice its quantity of water, extracted with chloroform, vigorously washed with water and dried over $MgSO_4$ and the chloroform is distilled off. 49 g of crude product are subjected to distillation.

Yield: 38.4 g (89.5% of the theory) of 1,4-dioxo-1-[4-chlorophenyl]-2-phenyl-pentane; B.p: 164° C/0.5 mm Hg; m.p. 64° C (ethanol)

$C_{17}H_{15}O_2Cl$ (186.76) Calculated: C, 71.20; H, 5.28; Cl, 12.36. Found: C, 71.53; H, 5.33.

EXAMPLE 6

A solution of 21.2 g (0.2 mol) of benzaldehyde and 100 ml of absolute dimethylformamide is added dropwise in the course of ½ hour to a mixture of 4.9 g (0.1 mol) of NaCN and 100 ml of absolute dimethylformamide in a manner analgous to Example 3. Stirring is then continued for 1½ hours at 35° C. A solution of 21.9 g (0.15 mol) of benzalacetone and 100 ml of dimethylformamide is then slowly added dropwise in the course of 3½ hours at 35° C. Stirring is then continued for 3½ hours at the same temperature. The reaction mixture is treated with twice its quantity of water and the product is worked up in a manner analogous to Example 5. 43.5 g of crude product are obtained from which 25.2 g of 1,4-dioxo-1,2-diphenyl-pentane (67% of theoretical) are obtained by distillation. B.p.: 166° C/0.4 mm Hg; m.p.: 60°–61° C $C_{17}H_{16}O_2$ (253.3) Calculated: C, 80.92; H, 6.39. Found: C, 80.62; H, 6.50.

EXAMPLE 7

A solution of 21.2 g (0.2 mol) of benzaldehyde and 75 ml of absolute DMSO is added dropwise in the course of ½ hour to a mixture of 0.98 g (0.02 mol) of NaCN or KCN and 75 ml of absolute dimethylsulphoxide in a manner analogous to Example 3. Stirring is continued for ½ hour at 35° C. A solution of 29.2 g (0.2 mol) of benzalacetone and 75 ml of absolute dimethylsulphoxide is then added dropwise in the course of ½ hour. Stirring is continued for ½ hour and the product is then worked up as in Example 5.

Yield: 37.3 g (69% of theoretical) of 1,4-dioxo-1,2-diphenylpentane.

EXAMPLE 8

A solution of 42.5 g (0.4 mol) of freshly distilled benzaldehyde and 125 ml of absolute dimethylformamide is slowly added dropwise to a mixture of 19.6 g of NaCN (0.4 mol) and 125 ml of dimethlformamide in a manner analogous to Example 3. The mixture is stirred at a reaction temperature of 35° C for 21 hours, during which time a creamy product forms. A solution of 34.3 g (0.3 mol) of ethyl crontonate and 150 ml of absolute dimethylformamide is then added dropwise at 35° C in the course of 2½ hours. Stirring is continued for a further 3 hours at the same temperature and the reaction mixture is then treated with twice its quantity of water and worked up as in Example 3.

The crude product is subjected to distillation. 23.8 g of β-benzoyl-butyric acid ethyl ester (36% of theoretical) are obtained. B.p.: 128° – 135° C/1.2 mm Hg.

EXAMPLE 9

A solution of 42.5 g (0.4 mol) of freshly distilled benzaldehyde and 125 ml of absolute dimethylformamide is added dropwise to a mixture of 19.6 g of NaCN (0.4 mol) and 125 ml of absolute dimethylformamide in a manner analogous to Example 3. Stirring is continued for 12 hours at 35° C. A solution of 51.6 (0.3 mol) of freshly distilled diethyl maleate and 150 ml of absolute dimethylformamide is added dropwise at 35° C in the course of 2 hours.

Stirring is then continued for a further 2 hours at the same temperature and the product is then worked up as in Example 5. The crude product is subjected to distillation, 27.5 g of benzoyl succinic acid ethyl ester (33% of the theory) being obtained.

Yield: 27.5 g (33% of theoretical); B.p: 150° – 160° C/0.8 mm Hg.

EXAMPLE 10

A solution of 56.2 g (0.4 mol) of p-chlorobenzaldehyde and 120 ml of absolute dimethylformamide is slowly added dropwise to a mixture of 9.8 g (0.2 mol) of NaCN and 200 ml of absolute dimethylformamide in a manner analogous to Example 3.

A solution of 51.6 g (0.3 mol) of freshly distilled diethylmaleate and 80 ml of absolute dimethylformamide is then added dropwise to this reaction mixture at 35° C in the course of 4 hours. Stirring is continued for 4 hours at the same temperature and the reaction mixture is then treated with twice the quantity of water and worked up as in Example 5.

The residue is subjected to distillation, which yields 32.5 g of p-chloro-benzoyl-succinic acid ethyl ester (34.5% of theoretical); b.p. 182° – 190° C/1 –2 torr.

EXAMPLE 11

A solution of 28.1 g (0.2 mol) of p-chlorobenzaldehyde and 100 ml of absolute ethanol is added dropwise in the course of ½ hour in a manner analogous to Example 3. Stirring is then continued for a further ½ hour at the same temperature.

A solution of 31.2 g (0.15 mol) of benzalacetophenone and 100 ml of absolute ethanol is then slowly added dropwise at 35° C in the course of 2 hours. Stirring is continued for a further 2 hours at the same temperature and the reaction mixture is then treated with twice its quantity of water and worked up as in Example 5.

57.1 g of crude product are obtained from which 42.6 g (80% of theoretical) of 1,4-dioxo-1-(p-chlorophenyl)-2,4-diphenyl-butane can be isolated as a white, crystalline product by crystallisation from ethanolic solution. M.p: 92° – 93° C.

EXAMPLE 12

27.2 g (0.2 mol) of p-methoxybenzaldehyde, 9.8 g (0.2 mol) of NaCN and 140 ml of absolute dimethylformamide are added together in a manner analogous to Example 3. The reaction mixture is stirred overnight at a reaction temperature of 70° C. It is then cooled to 35° C and a solution of 5.3 g (0.1 mol) of freshly distilled acrylonitrile and 70 ml of absolute dimethylformamide is then added dropwise in the course of one hour at the same temperature. Stirring is continued at the same temperature for one hour and the reaction mixture is then treated with twice its quantity of water and worked up as in Example 5.

The crude product is subjected to distillation, which yields 11.4 g of β-(4-methoxybenzoyl)-propionitrile (60.4% of theoretical).

B.p: 196° – 198° C/0.6 mm Hg; M.p: 94° C.

EXAMPLE 13

A solution of 38.4 g (0.4 mol) of freshly distilled furfurol and 100 ml of absolute dimethylformamide is added dropwise in the course of 45 minutes to a mixture of 9.8 g (0.2 mol) of NaCN and 200 ml of absolute dimethyl formamide at 35° C in a manner analogous to Example 3. Stirring is then continued for 15 minutes. A solution of 15.9 g (0.3 mol) of freshly distilled acrylonitrile is then added dropwise in the course of one hour at 35° C. The reaction mixture is stirred for a further 1¼ hours at the same temperature and twice its quantity of water is then added. Since the reaction product cannot be extracted very thoroughly with chloroform, it is carefully acidified with dilute sulphuric acid and worked up as described in Example 5.

The reaction product is subjected to distillation, 13.6 g of β-furoyl-propionitrile (32% of theoretical) being obtained.

B.p: 133° – 136° C/1 mm Hg; M.p: 76° C.

EXAMPLE 14

A solution of 38.4 g (0.4 mol) of freshly distilled furfurol and 125 ml of absolute dimethylformamide is added dropwise to a mixture of 9.8 g (0.2 mol) of NaCN and 125 ml of absolute dimethylformamide at 35° C in the course of 45 minutes in a manner analogous to Example 3. Stirring is then continued for ½ hour at 35° C. A solution of 43.8 g (0.3 mol) of benzalacetone and 150 ml of absolute dimethylformamide is then added dropwise in the course of 1½ hours. Stirring is continued at the same temperature for a further 1½ hours and the reaction mixture is then treated with twice its quantity of water and worked up as described in Example 5. 32.1 g of 1,4-dioxo-1-furyl-2-phenyl-pentane (44% of theoretical) are isolated from 83.5 g of the crude product by distillation; b.p. 147°–148° C/0.4 torr.

EXAMPLE 15

A solution of 19.2 g (0.2 mol) of freshly distilled furfurol and 100 ml of absolute dimethylformamide are added dropwise in the course of one hour at 35° C to a mixture of 4.9 g (0.1 mol) of NaCN and 100 ml of absolute dimethyl formamide in a manner analogous to Example 3. Stirring is continued for a further ½ hour at 35° C. A solution of 31.2 g (0.15 mol) of benzal acetophenone and 100 ml of absolute dimethylformamide is then added dropwise in the course of 2 hours. Stirring is continued for 2 hours at the same temperature and the reaction mixture is then treated with twice its quantity of water and worked up as in Example 5.

51.2 g of crude product are obtained, from which 38.8 g of 1,4-dioxo-1-furyl-2,4-diphenylbutane (84.5% of theoretical) are isolated by crystallisation from ethanolic solution.

M.p: 115°–116° C.

$C_{20}H_{16}O_3$ (304.33) Calculated: C, 78.93; H, 5.30. Found: C, 79.11; H, 5.49.

EXAMPLE 16

A solution of 42.5 g (0.4 mol) of freshly distilled benzaldehyde and 125 ml of absolute dimethylformamide is slowly added dropwise to a mixture of 19.6 g (0.4 mol) of NaCN and 125 ml of absolute dimethylformamide in a manner analogous to Example 3. Stirring is then continued at a reaction temperature of 35° C for 2 hours, during which time a creamy product is formed.

A solution of 52.8 g (0.3 mol) of ethyl cinnamate and 150 ml of absolute dimethylformamide is then added dropwise at 35° C in the course of 3 hours. Stirring is continued for a further 3 hours at the same temperature and the product is worked up as in Example 5.

12.6 g of 4-oxo-3,4-diphenyl-butyric acid ethyl ester (15% of theoretical) are isolated from the crude product by distillation: b.p. 170°–175° C/0.7 torr.

EXAMPLE 17

A solution of 21.2 g (0.2 mol) of benzaldehyde and 100 ml of absolute dimethylformamide is added dropwise in the course of ½ hour to a mixture of 9.8 g (0.2 mol) of NaCN and 100 ml of absolute dimethylformamide in a manner analogous to Example 3. Stirring is continued for 2½ hours at 35° C. A solution of 26.6 g (0.15 mol) of dimethyl-$\beta$-benzoyl-ethylamine and 100 ml of absolute dimethylformamide is then slowly added dropwise in the course of 2 hours. Stirring is continued for 2 hours at the same temperature and water is then added to the reaction mixture in three times its quantity. The reaction product precipitates immediately. After cooling in an ice bath, the precipitated product is suction filtered and thoroughly washed with water. 34.3 g of crude product are isolated. 21.6 g (60.5% of the theory) of dibenzoyl ethane are isolated by recrystallisation from ethanol; m.p. 143° C.

EXAMPLE 18

A solution of 21.2 g (0.2 mol) of freshly distilled benzaldehyde and 100 ml of absolute dimethylformamide is added dropwise in the course of ½ hour to a mixture of 9.8 g (0.2 mol) of NaCN and 100 ml of absolute dimethylformamide in a manner analogous to Example 3. Stirring is then continued for ½ hour at 35° C. A solution of 19.8 g (0.15 mol) of phenyl vinyl ketone and 100 ml of absolute dimethylformamide is then slowly added dropwise at 35° C in the course of 2 hours.

Stirring is then continued for one more hour at the same temperature and water is added to the reaction mixture in three times its quantity and the product is worked up as in Example 17. 35.2 g of crude product are obtained.

Yield: 23.5 g (65.5% of theoretical) of dibenzoylethane; M.p: 143° C.

EXAMPLE 19

A solution of 5.35 g (0.05 mol) of pyridine aldehyde-(2) and 30 ml of absolute dimethylformamide is added dropwise in the course of 45 minutes to a mixture of 2.45 g(0.05 mol) of NaCN and 30 ml of absolute dimethylformamide in a manner analogous to Example 3. Stirring is then continued for 1¼ hours at the same temperature. A solution of 7.9 g (0.038 mol) of benzal acetophenone and 40 ml of absolute dimethylformamide is then added dropwise in the course of 2 hours. The reaction mixture is then stirred for 2 hours at the same temperature and twice its quantity of water is added and the reaction product is worked up as in Example 5.

8.1 g of 1,4-dioxo-1-(pyridyl-2)-2,4-diphenylbutane (67.5% of theoretical) are isolated from 12.9 g of crude product by fractional crystallisation from ethanol; m.p. 95°–96° C $C_{21}H_{17}NO_2$ (315.35) Calculated: C, 79.98; H, 5.49; N, 4.44. Found C, 80.15; H, 5.67; N, 4.45.

EXAMPLE 20

A solution of 5.35 g (0.05 mol) of pyridine aldehyde-(3) and 30 ml of absolute dimethylformamide is added dropwise in the course of ½ hour at 35° C to a mixture of 2.45 g (0.05 mol) of NaCN and 30 ml of absolute dimethylformamide in a manner analogous to Example 3. Stirring is then continued for 2½ hours at the same temperature.

A solution of 6.73 g (0.038 mol) of dimethyl-$\beta$-benzoylethylamine and 40 ml of absolute dimethylformamide is then added dropwise in the course of one hour. Stirring is continued for 3 hours at the same temperature and the reaction mixture is then treated with twice its quantity of water and worked up as in Example 5.

9.6 g of crude product are obtained and subjected to distillation. 3.2 g of 1,4-dioxo-1-(pyridyl-3)-4-phenyl-butane (35% of theoretical) are obtained.

B.p: 205°–215° C/0.4 mm Hg; M.p: 102°–103° C (ethanol)

EXAMPLE 21

2 g (approximately 0.04 mol) of sodium cyanide are added to a solution of 23.5 g (0.4 mol) of freshly distilled benzaldehyde in 320 ml of dimethylformamide (absolute) in a 500 ml 4-necked flask equipped with stirrer, dropping funnel, KOH drying tube and internal thermometer.

The reaction temperature rises from 25° to 30° C in the course of 15 minutes and the mixture turns yellowish green. A solution of 15.9 g (0.3 mol) of acrylonitrile and 80 ml of dimethylformamide (absolute) is the introduced dropwise into the reaction mixture in the course of one hour at 30° C. After a further 75 minutes, the reaction mixture is poured into 800 ml of water and vigorously shaken. It is then extracted twice with 200 ml of chloroform and twice with 100 ml of chloroform. The chloroform extracts are thoroughly washed with water and dried over $Na_2SO_4$ and the chloroform is distilled off. The brown residue is subjected to vacuum distillation; B.p. 135°–140° C/0.1 mm Hg. The distillate is then recrystallised from ethanol. 24.3 g (51% of theoretical) of $\beta$-benzoyl-propionitrile are thereby obtained in the form of colourless crystals, m.p. 74° C.

EXAMPLE 22

A solution of 14.05 g (0.1 mol) of freshly distilled p-chlorobenzaldehyde and 50 ml of anhydrous dimethylformamide is added dropwise in the course of 10 minutes at 35° C to a mixture of 2.4 g (0.05 mol) of sodium cyanide and 50 ml of dimethylformamide with stirring. Stirring is continued for 5 minutes and thereafter a solution of 4.0 g (0.075 mol) of freshly distilled acrylonitrile and 100 ml of dimethylformamide is added dropwise in the course of 20 minutes at 35° C. Stirring is carried out for another 3 hours at the same temperature and the reaction mixture is then treated with twice its quantity of water. Then after the reaction mixture is extracted several times with chloroform and the combined organic extracts first washed with dilute aqueous sulphuric acid with a pH value of 2, then with aqueous sodium hydrogen carbonate solution and finally with water. The solvent is distilled off and the residue is fractionally distilled in vacuo. Yield: 13.2 g (91% of the theory) of 4-oxo-4-(p-chloro-phenyl)- butyric acid nitrile; b.p. 137° C/0.25 mm Hg; m.p. 73° C (recrystallized from ethanol).

EXAMPLE 23

From 14.05 g (0.05 mol) of 4,4'-dichloro-benzoin and 4.0 g (0.075 mol) of freshly distilled acrylonitrile there are obtained in accordance with the method described in Example 22, 2.8 g (89% of the theory) of 4-oxo-4-(p-chloro-phenyl)-butyric acid nitrile; b.p. 137° C/0.25 mm Hg; m.p. 73° C (recrystallized from ethanol).

EXAMPLE 24

A solution of 4.62 g (25 mmol) of freshly distilled p-bromobenzaldehyde in 30 ml of dimethylformamide is added dropwise within 10 minutes to a mixture of 0.6 g (12.5 mmol) of sodium cyanide and 30 ml of dimethylformamide. Stirring is continued for 5 minutes at the same temperature and a solution of 1 g of freshly distilled acrylonitrile in 60 ml of dimethylformamide is then added dropwise at 35° C in the course of 20 minutes. Stirring is continued for a further 3 hours at the same temperature and the reaction mixtures then treated with twice its quantity of water. The reaction product is then isolated as described in Example 22. Yield: 3.6 g (81% of the theory) of 4-oxo-4-(p-bromophenyl)-butyric acid nitrile; b-p. 150°–151° C/0.3 mm Hg. m.p. 96° C (recrystallized from isopropanol).

$C_{10}H_8BrNO$ (238) Calculated: C, 50.44; H, 3.39; N, 5.89. Found: C, 50.65; H, 3.65; N, 5.89. Mol. mass 236.1 (osmometrically in chloroform).

EXAMPLE 25

According to the method described in Example 22, a solution of 5.2 g (33 mmol) of freshly distilled naphthaldehyde-(2) and 30 ml of dimethylformamide is added dropwise to a mixture of 0.8 g (16.5 mmol) of sodium cyanide and 30 ml of dimethylformamide. After further adding a solution of 1.4 g (25 mmol) of freshly distilled acrylonitrile in 60 ml of dimethyl formamide, the reaction mixture is worked up as in Example 22. Yield: 4.23 g (81% of the theory) of 4-oxo-4-[naphthyl-(2)]-butyric acid nitrile; b.p. 179°–180° C/0.3 mm Hg; m.p. 116° C (recrystallized from ethanol).

EXAMPLE 26

A solution of 5.35 g (50 mmol) of freshly distilled pyridine aldehyde-(3) in 50 ml of dimethylformamide is added dropwise at 35° C in the course of 10 minutes whilst stirring to a mixture of 2.45 g (50 mmol) of sodium cyanide and 50 ml of dimethylformamide. Stirring is continued for 5 minutes at this temperature and a solution of 2.0 g (38 mmol) of freshly distilled acrylonitrile in 100 ml of dimethylformamide is then added dropwise in the course of 20 minutes at 35° C. Stirring is continued at the same temperature for 3 hours, the reaction mixture then treated with twice its quantity of water and dilute aqueous sulphuric acid added until the pH value of the reaction mixture is 2–3. After this the reaction mixture is neutralised with sodium hydrogen carbonate and the aqueous reaction mixture perforated for 24 hours with chloroform. The resultant chloroform extract is concentrated by distilling off the chloroform and the remaining crude reaction product fractionally distilled in vacuo. Yield: 5.4 g (89% of the theory) of 4-oxo-4-[pyridyl-(3)]-butyric acid nitrile; b.p. 148°–149° C/0.15 mm Hg; m.p. 73° C (recrystallized from isopropanol).

$C_9H_8N_2O$ (160.2) Calculated: C, 67.48; H, 5.03; N, 17.49. Found: C, 67.40; H, 4.86; N, 17.39. Mol. mass 162.4 (osmometrically in acetone).

EXAMPLE 27

From 5.35 g (50 mmol) of freshly distilled pyridine aldehyde-(4) and 2.0 g (38 mmol) of freshly distilled acrylonitrile there are obtained in accordance with the method described in Example 26, 4.25 g (71% of the theory) of 4-oxo-4-[pyridyl-(4)]-butyric acid nitrile; b.p. 129°–132° C/0.15 mm Hg, m.p. 53° C (recrystallized from ligroin and isopropanol).

$C_9H_8N_2O$ (160.2) Calculated: C, 67.48; H, 5.03; N, 17.49. Found: C, 67.49; H, 5.08; N, 17.35. Mol. mass 162.9 (osmometrically in acetone).

EXAMPLE 28

A solution of 11.2 (0.1 mol) of thiophene aldehyde-(2) (freshly distilled) in 50 ml of dimethylformamide is added dropwise at 35° C in the course of 30 minutes whilst stirring to a mixture of 2.45 g (0.05 mol) of sodium cyanide and 50 ml of dimethylformamide. Stirring is continued for 30 minutes and then a solution of 4 g (0.075 mol) of freshly distilled acrylonitrile added dropwise in the course of 2½ hours at 35° C. Stirring is then carried out at the same temperature for another 3 hours and the reaction mixture then worked up as described in Example 22. Yield: 10.5 g (85% of the theory) of 4-oxo-4-[thienyl-(2)]butyric acid nitrile; b.p. 118°–119° C/0.2 mm Hg, m.p. 67° C (recrystallized from isopropanol).

EXAMPLE 29

A solution of 24 g (0.2 mol) of p-tolylaldehyde in 70 ml of dimethylformamide is added dropwise at 40° C in the course of 3 hours whilst stirring to a mixture of 9.8 g (0.2 mol) of sodium cyanide and 70 ml of dimethylformamide. Stirring is continued for 12 hours at the same temperature and a solution of 8.0 g (0.15 mol) of freshly distilled acrylonitrile in 70 ml of dimethylformamide added dropwise in the course of 8 hours at 35° C. Stirring is carried out for a further 4 hours at the same temperature and the reaction mixture then worked up as in Example 22. Yield: 11.2 g (43% of the theory) of 4-oxo-4-(4-methyl-phenyl)-butyric acid nitrile; b.p. 129°–131° C/0.4 mm Hg, m.p. 75° C (recrystallized from isopropanol).

EXAMPLE 30

From 12.02 g (0.05 mol) of 4,4'-dimethyl-benzoin and 4 g of freshly distilled acrylonitrile there are obtained in accordance with the method described in Example 22, 9.1 g (70% of the theory) of 4-oxo-4-(4-methyl-phenyl)-butyric acid nitrile; b.p. 129°–131° C/0.4 mm Hg, m.p. 73° C (recrystallized from isopropanol).

EXAMPLE 31

From 13.6 g (0.05 mol) of 4,4'-dimethoxy-benzoin (anisoin) and 4 g of freshly distilled acrylonitrile there are obtained in accordance with the method described in Example 22, 7.7 g (53.5% of the theory) of 4-oxo-4-(4-methoxy-phenyl)-butyric acid nitrile; b.p. 160°–162° C/02. mm Hg, m.p. 93° C (recrystallized from isopropanol).

EXAMPLE 32

A solution of 42.4 g (0.4 mol) of freshly distilled benzaldehyde in 100 ml of dimethylformamide is added dropwise at 35° C in the course of an hour whilst stirring to a mixture of 2 g (0.04 mol) of sodium cyanide and 200 ml of dimethylformamide. Stirring is continued for one hour at the same temperature and a solution of 20.1 g (0.3 mol) of freshly distilled methacrylonitrile then added dropwise at 35° C in the course of 2½ hours. Stirring is carried out for further 3 hours at the same temperature and the reaction mixture then worked up as described in Example 22. Yield: 38.0 g (73% of the theory) of 4-oxo-4-phenyl-2-methyl-butryic acid nitrile; b.p. 123+ C/0.5 mm Hg, m.p. 44° C (recrystallized from isopropanol).

$C_{11}H_{11}NO$ (173.2) Calculated: C, 76.27; H, 6.40; N, 8.09. Found: C, 76.25; H, 6.33; N, 8.09. Mol. mass 174.7 (osmometrically in chloroform).

EXAMPLE 33

From 42.4 g (0.4 mol) of freshly distilled benzaldehyde and 20.1 g (0.3 mol) of crotonic acid nitrile there are obtained in accordance with the method described in Example 32, 36.9 g (71% of the theory) 4-oxo-4-phenyl-3-methyl-butryic acid nitrile; b.p. 103°–104° C/0.15 mm Hg, m.p. 60° C (recrystallized from isopropanol)

$C_{11}H_{11}NO$ (173.2) Calculated: C, 76.27; H, 6.40; N, 8.09. Found: C, 76.43; H, 6.28; N, 8.25. Mol. mass 172 (osmometrically in acetone).

EXAMPLE 34

According to the method described in Example 22 a solution of 10.6 g (0.1 mol) of freshly distilled benzaldehyde in 50 ml of dimethylformamide are added dropwise in the course of an hour to a mixture of 2.4 g of sodium cyanide and 50 ml of dimethylformamide. Stirring is continued for a further 2 hours and thereafter a solution of 9.7 g (0.75 mol) of cinnamic acid nitrile and 100 ml of dimethylformamide added dropwise in the course of 6 hours. After another 6 hours' stirring the reaction mixture is worked up as in Example 22. Yield: 14.1 g (80% of the theory) of 4-oxo-3,4-diphenyl-butyric acid nitrile; b.p. 161° C/0.3 mm Hg., m.p. 85° C (recrystallized from isopropanol).

$C_{16}H_{13}NO$ (235.3) Calculated: C, 81.68; H, 5.57; N, 5.95. Found: C, 81.83; H, 5.56; N, 5.95. Mol. mass 238.8 (osmometrically in acetone).

EXAMPLE 35

A solution of 21.6 g (0.2 mol) of freshly distilled benzaldehyde in 50 ml of dimethylformamide is added dropwise at 35° C in the course of 10 minutes whilst stirring to a mixture of 4.9 g (0.1 mol) of sodium cyanide and 50 ml of dimethylformamide. Stirring is continued for 5 minutes at the same temperature and a solution of 10.6 g (0.15 mol) of freshly distilled methylvinylketone in 100 ml of dimethylformamide added dropwise at 35° C in the course of 20 minutes. Stirring is carried out for a further 1 hour at the same temperature and the reaction mixture then treated with twice its quantity of water. The reaction mixture is thereafter extracted several times with chloroform; the combined organic extracts are first washed with dilute aqueous sulphuric acid and with a pH value of 2, then with aqueous sodium hydrogen carbonate solution and finally with water. After the solvent has been distilled off, the residue of the extracts is fractionally distilled in vacuo. Yield: 21.2 g (80% of the theory) 1,4-dioxo-1-phenyl-pentane; b.p. 92°–93° C/0.1 mm Hg.

EXAMPLE 36

From 28.1 g (0.2 mol) of freshly distilled p-chloro-benzaldehyde and 10.6 g (0.15 mol) of freshly distilled methylvinylketone there are obtained in accordance with the method described in Example 35, 25.3 g (80% of the theory) of 1,4-dioxo-1-(4-chloro-phenyl)-pentane; b.p. 118°–120° C (0.2 mm Hg; m.p. 74°–75° C (recrystallized from isopropanol).

What is claimed is:

1. Process for preparing ketones which comprises contacting in the presence of a cyanide ion:

A. an unsaturated compound having the formula (I):

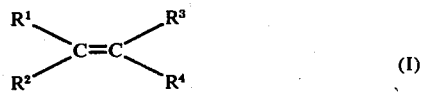

wherein $R^1$, and $R^2$ and $R^3$ are the same or different and are selected from the group of hydrogen, unsubstituted aliphatic having up to 12 carbon atoms, unsubstituted cycloaliphatic having up to 18 carbon atoms, unsubstituted araliphatic having up to 18 carbon atoms where the aryl portion is naphthyl or phenyl and the alkyl portion contains up to 6 carbon atoms, unsubstituted phenyl or naphthyl, unsubstituted heterocyclic groups having 5 or 6 members in the groups including heterocyclic groups containing a condensed benzene group where the hetero-atom is oxygen, nitrogen or sulfur and carboxylic acid ester and substituted components thereof where the substituent is a halogen atom, a cyano group, a nitro group, a mono- or di-substituted or unsubstituted amino group, an alkyl group having up to 6 carbon atoms, a phenyl group, hydroxyl, alkoxy, alkylthio, carboxylic acid ester and a thiocarboxlyic acid ester group with up to 6 carbon atoms, alkylcarbonyl, arylcarbonyl, alkylthiocarbonyl or arylthiocarbonyl group and $R^4$ is nitrile (CN), —CO—$R^5$ or —CO—O$R^5$ wherein $R^5$ is selected from the group of unsubstituted aliphatic having up to 12 carbon atoms, unsubstituted cycloaliphatic having up to 18 carbon atoms, unsubstituted araliphatic having up to 18 carbon atoms where the aryl portion is naphthyl or phenyl and the alkyl portion is up to 6 carbon atoms, phenyl, naphthyl, a 5 or 6 member heterocyclic group including heterocyclic groups containing a condensed benzyl group, a carboxylic acid group and substituted groups thereof where the substituents are selected from the group consisting of a halogen atom, a nitro group, a cyano group, an unsubstituted mono- or di-substituted amino group, an alkyl group containing up to 6 carbon atoms, a phenyl group a hydroxyl group, an alkoxy group, an alkylthio group, a carboxylic acid ester group having up to 6 carbon atoms, a thiocarboxylic acid ester group having up to 6 carbon atoms, an alkylcarbonyl group, an arylcarbonyl group, an alkylthiocarbonyl group and an arylthiocarbonyl group and $R^1$, $R^2$ and/or $R^1$ and $R^3$ and/or $R^2$ and $R^5$ or $R^3$ and $R^5$ together with the carbon atoms to which they are attached as substituents can form a carboxylic or heterocyclic ring, or B. a Mannich base having the formula

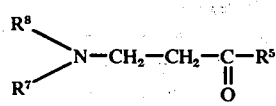

wherein

R⁵ is an unsubstituted aliphatic having up to 12 carbon atoms, unsubstituted cycloaliphatic having up to 18 carbon atoms, unsubstituted araliphatic having up to 18 carbon atoms where the aryl portion is naphthyl or phenyl and the alkyl portion contains up to 6 carbon atoms, unsubstituted phenyl or naphthyl, unsubstituted heterocyclic groups having 5 or 6 members in the groups including heterocyclic groups containing a condensed benzene group where the hetero atom is oxygen, nitrogen or sulfur and substituted components of said aliphatic, cycloaliphatic, araliphatic, phenyl, naphthyl or heterocyclic groups where the substituent is a halogen atom, a cyano group, a nitro group, a mono or di-substituted or unsubstituted amino group, an alkyl group having up to 6 carbon atoms, a phenyl group, hydroxyl, alkoxy, alkylthio, carboxylic acid ester and a thiocarboxylic acid ester group with up to 6 carbon atoms, alkylcarbonyl, arylcarbonyl, alkylthiocarbonyl or arylthiocarbonyl groups;

R⁷ and R⁸ are each independently aliphatic having up to 12 carbon atoms or together with the nitrogen atom of said Mannich base form a 5 or 6 membered ring, with:

C. an aromatic or heterocyclic aldehyde; or

D. a benzoin having the formula

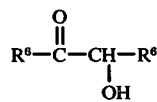

wherein

R⁶ is a substituted or unsubstituted naphthyl or phenyl group or a 5 or 6 member heterocyclic group where the hetero atom is oxygen, sulfur or nitrogen.

2. Process of claim 1 wherein said benzoin is reacted.

3. Process of claim 1 wherein the compound corresponding to Formula I is a α,β-unsaturated ketone having the following formula:

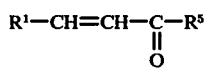

herein

R¹ is selected from the group of hydrogen, optionally substituted aliphatic, cycloaliphatic, araliphatic, aromatic, heterocyclic and carboxylic acid ester and R⁵ is selected from the group of optionally substituted aliphatic, cycloaliphatic, araliphatic, aromatic and heterocyclic.

4. Process of claim 1 wherein said Mannich base is reacted.

5. Process of claim 1 carried out in a polar solvent.

6. Process of claim 1 wherein the cyanide ion is used in the form of sodium or potassium cyanide.

7. Process of claim 6 wherein the sodium or potassium cyanide is used in an equimolar quantity based on the quantity of the aldehyde.

8. Process according to claim 1 wherein said aromatic or heterocyclic aldehyde has the formula

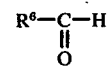

wherein

R⁶ is a substituted or unsubstituted aromatic or 5 or 6 membered heterocyclic group and where substituted is substituted by a halogen a atom, a cyano group, a nitro group a mono- or di-substituted or unsubstituted amino group, an alkyl group having up to 6 carbon atoms, a phenyl group, hydroxyl, alkoxy, alkylthio, carboxylic acid ester and a thiocarboxylic acid ester group with up to 6 carbon atoms, alkylcarbonyl, aryl carbonyl, alkylthiocarbonyl or arylthiocarbonyl groups.

9. Process for preparing ketones which comprises contacting in the presence of a cyanide ion:

A. an unsaturated compound having the formula (I):

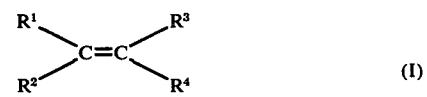

(I)

wherein R¹, R² and R³ are the same or different and are selected from the group of hydrogen, unsubstituted alkyl having up to 12 carbon atoms, unsubstituted cycloaliphatic having up to 18 carbon atoms, unsubstituted araliphatic having up to 18 carbon atoms where the aryl portion is naphthyl or phenyl and the alkyl portion contains up to 6 carbon atoms, unsubstituted phenyl or naphthyl, unsubstituted heterocyclic groups having 5 or 6 members in the groups including heterocyclic groups containing a condensed benzene group where the heteroatom is oxygen, nitrogen or sulfur and carboxylic acid ester and substituted components of said alkyl, cycloaliphatic, araliphatic, phenyl, naphthyl or heterocyclic groups where the substituent is a halogen atom, a cyano group, a nitro group, a mono or di-substituted or unsubstituted amino group, an alkyl group having up to 6 carbon atoms, a phenyl group, hydroxyl, alkoxy, alkylthio, carboxylic acid ester and a thiocarboxylic acid ester group with up to 6 carbon atoms, alkylcarbonyl, arylcarbonyl, alkylthiocarbonyl or arylthiocarbonyl group and R⁴ is nitrile (CN), —CO—R⁵ or —CO—OR⁵ wherein R⁵ is selected from the group of unsubstituted aliphatic having up to 12 carbon atoms, unsubstituted cycloaliphatic having up to 18 carbon atoms, unsubstituted araliphatic having up to 18 carbon atoms where the aryl portion is naphthyl or phenyl and the alkyl portion is up to 6 carbon atoms, phenyl, naphthyl, a 5 or 6 member heterocyclic group including heterocyclic groups containing a condensed benzyl group, a carboxylic acid group and substituted groups thereof where the substituents are selected from the group consisting of a halogen atom, a nitro group, a cyano group, an unsubstituted mono- or di-substituted amino group, an alkyl group containing up to 6 carbon atoms, a phenyl group a hydroxyl group, an alkoxy group, an alkylthio group, a carboxylic acid ester group having up to 6 carbon atoms, a thiocarboxylic acid ester group having up to 6 carbon atoms, an alkylcarbonyl group, an arylcarbonyl group, an alkylthiocarbonyl group and an arylthiocarbonyl group and $R^1$, $R^2$ and/or $R^1$ and $R^3$ and/or $R^2$ and $R^5$ or $R^3$ and $R^5$ together with the carbon atoms to which they are attached as substituents can form a carboxylic or heterocyclic ring, or B. a Mannich base having the formula

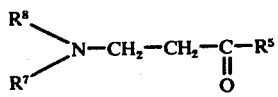

wherein
$R^5$ is an unsubstituted aliphatic having up to 12 carbon atoms, unsubstituted cycloaliphatic, having up to 18 carbon atoms, unsubstituted araliphatic having up to 18 carbon atoms where the aryl portion is naphthyl or phenyl and the alkyl portion contains up to 6 carbon atoms, unsubstituted phenyl or naphthyl, unsubstituted heterocyclic groups having 5 to 6 members in the groups including heterocyclic groups containing a condensed benzene group where the hetero atom is oxygen, nitrogen or sulfur and substituted components thereof where the substituent is a halogen atom, a cyano group, a nitro group, a mono or di-substituted or unsubstituted amino group, an alkyl group having up to 6 carbon atoms, a phenyl group, hydroxyl, alkoxy, alkylthio, carboxylic acid ester and a thiocarboxylic acid ester group with up to 6 carbon atoms, alkylcarbonyl, arylcarbonyl, alkylthiocarbonyl or arylthiocarbonyl groups;

$R^7$ and $R^8$ are each independently aliphatic having up to 12 carbon atoms or together with the nitrogen atom of said Mannich base form a 5 or 6 membered ring, with:

C. an aromatic or heterocyclic aldehyde; or
D. a benzoin having the formula

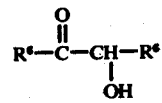

wherein
$R^6$ is a substituted or unsubstituted naphthyl or phenyl group or a 5 or 6 member heterocyclic group where the hetero atom is oxygen, sulfur or nitrogen.

* * * * *

UNITED STATES PATENT AND TRADEMARK OFFICE
CERTIFICATE OF CORRECTION

PATENT NO. : 4,014,889        Page 1 of 2 pages
DATED : March 29, 1977
INVENTOR(S) : Hermann Stetter et al It is certified that error appears in the above-identified patent and that said Letters Patent are hereby corrected as shown below:

Insert:

--[30], Foreign Application Priority Data
  December 20, 1972    Germany........2262343 --.

Column 2, line 48, "the" should read -- The --.

Column 6, line 68, delete "14" and insert -- — --.

Column 8, line 15, after "5.33" insert -- Cl --.

Column 8, line 33, "(253.3)" should read -- (252.3) --.

Column 12, line 34, "the" should read -- then --.

Column 12, line 61, "Then after" should read -- Thereafter --.

Column 14, line 67, "C/02." should read -- C/0.2 --.

Column 15, line 11, before "further" insert -- a --.

Column 15, line 15, "123+" should read -- 123° --.

Column 15, line 66, delete "and" before "with" (first occurrence).

Column 16, line 61 (Claim 1), after "phenyl group" insert -- , --.

Column 17, line 53 (Claim 3), "onding" should read -- ponding --.

Column 17, line 54 (Claim 3), "aving" should read -- having --.

UNITED STATES PATENT AND TRADEMARK OFFICE
CERTIFICATE OF CORRECTION

PATENT NO. : 4,014,889

DATED : March 29, 1977

INVENTOR(S) : Hermann Stetter et al

It is certified that error appears in the above-identified patent and that said Letters Patent are hereby corrected as shown below:

Column 17, line 61, "herein" should read -- wherein --.

Column 18, line 19, "a halogen a atom" should read -- a halogen atom --.

Column 18, line 21, after "nitro group" insert -- , --.

Signed and Sealed this

Twenty-eighth Day of June 1977

[SEAL]

*Attest:*

RUTH C. MASON
*Attesting Officer*

C. MARSHALL DANN
*Commissioner of Patents and Trademarks*